United States Patent [19]
Dickinson et al.

[11] Patent Number: 5,465,726
[45] Date of Patent: Nov. 14, 1995

[54] ULTRASOUND IMAGING AND CATHETERS FOR USE THEREIN

[75] Inventors: Robert J. Dickinson, London; Richard I. Kitney, Fulham, both of United Kingdom

[73] Assignee: Intravascular Research Limited, London, United Kingdom

[21] Appl. No.: 256,955

[22] PCT Filed: Jan. 28, 1993

[86] PCT No.: PCT/GB93/00188

§ 371 Date: Jul. 27, 1994

§ 102(e) Date: Jul. 27, 1994

[87] PCT Pub. No.: WO93/15419

PCT Pub. Date: Aug. 5, 1993

[30] Foreign Application Priority Data

Jan. 30, 1992 [GB] United Kingdom ............... 9201983

[51] Int. Cl.[6] .................................................. A61B 8/12
[52] U.S. Cl. ............................. 128/663.01; 128/662.06
[58] Field of Search ..................... 128/662.03, 662.05, 128/662.06, 663.01

[56] References Cited

U.S. PATENT DOCUMENTS

| | | |
|---|---|---|
| 3,028,752 | 4/1962 | Bacon . |
| 3,938,502 | 2/1976 | Bom . |
| 4,142,412 | 3/1979 | McLeod et al. . |
| 4,546,771 | 10/1985 | Eggleton et al. . |
| 4,899,757 | 2/1990 | Pope, Jr. et al. . |
| 5,081,993 | 1/1992 | Kitney et al. . |
| 5,156,144 | 10/1992 | Iwasaki et al. ............... 128/660.03 |
| 5,257,629 | 11/1993 | Kitney et al. . |

FOREIGN PATENT DOCUMENTS

| | | |
|---|---|---|
| 0144761 | 6/1985 | European Pat. Off. . |
| 2173115 | 10/1973 | France . |
| 2014311 | 8/1979 | United Kingdom . |

Primary Examiner—George Manuel
Attorney, Agent, or Firm—Richard M. Goldberg

[57] ABSTRACT

A catheter having an ultrasonic transducer array at its distal end is constructed to overcome the "ringdown" problem by having a conically shaped reflecting interface space from an ultrasonic transducer array in such a way that the "dead space" is contained wholly within the catheter.

19 Claims, 1 Drawing Sheet

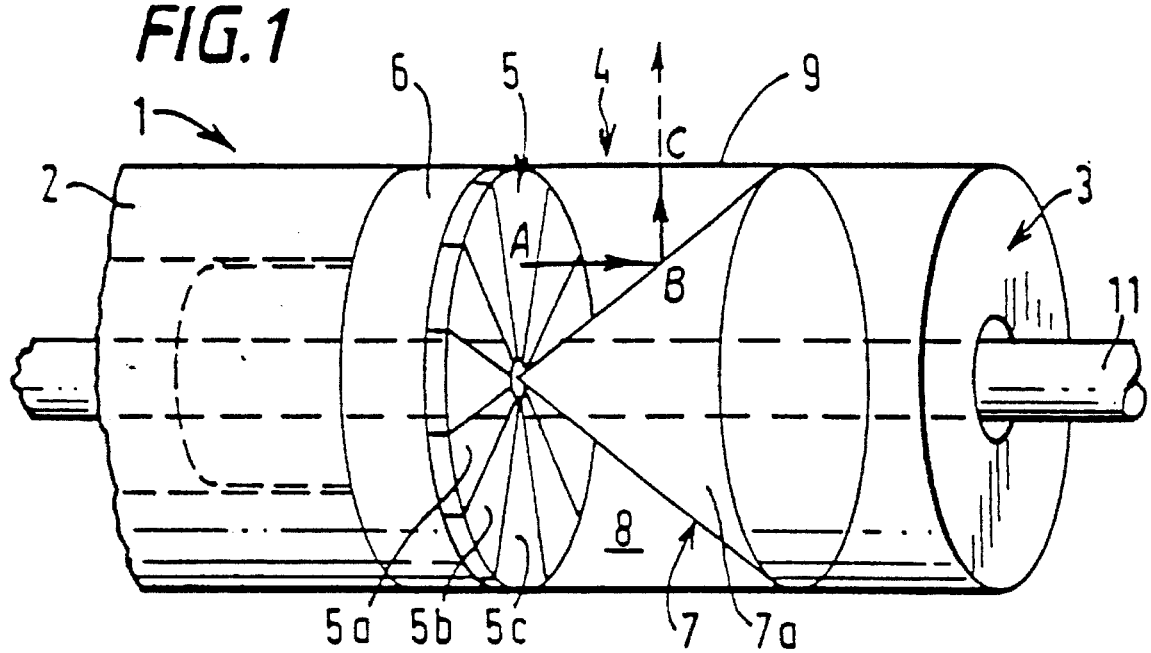
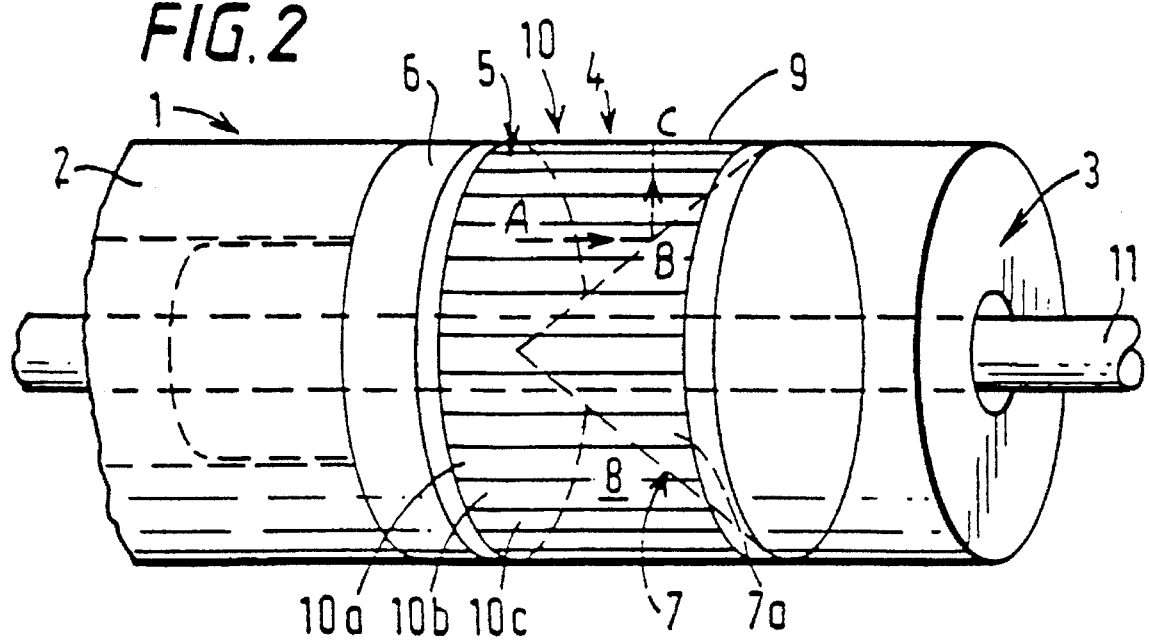

ULTRASOUND IMAGING AND CATHETERS FOR USE THEREIN

The present invention relates to medical ultrasound imaging and to catheters for use therein.

Our International Patent Application Nos. GB88/00971 (Publication No. WO89/04142) and GB90/00830 (Publication No. WO90/14601) disclose ultrasound systems for producing 3-dimensional and 2-dimensional images respectively of human internal organs and to catheters for use with such systems.

In these systems a catheter is provided at its distal end, with a piezo-electric transducer crystal array for generating ultrasonic signals and for receiving their echoes from which a visual representation is obtained.

Typically, such catheters are designed for insertion into an artery of the patient and the 2-dimensional and/or 3-dimensional images obtained are of the interior of the artery.

There is a problem with such ultrasound arrangements in that a dead space or blind spot, as far as the imaging is concerned, exists in the immediate vicinity of the transducer array. This caused by the fact that the mechanical vibration of the transducer elements to produce the ultrasonic signals takes some time to die down after an energisation pulse. This time is sufficiently long for the energisation vibration to interfere with the vibration of the crystal caused by the returning echo signal. This phenomena is sometimes referred to as "ringdown". The time it takes for the transducer element to stop vibrating as a result of its initial energisation is also sometimes referred to as the "ringdown" time.

This phenomenon is described, for example, in U.S. Pat. No. 4,899,757 and one solution to the "ringdown" problem is disclosed in that patent.

The arrangement disclosed in U.S. Pat. No. 4,899,757 deals with this "ringdown" problem by including the "dead space" within the catheter itself. In other words the initial path of the outgoing ultrasound signal and the final part of the path of the incoming echo signal are both contained within the catheter itself. It is thus possible with such an arrangement for any target, such as the interior wall of a blood vessel, to be visualised even though that target is immediately adjacent to or in contact with the external surface of the catheter.

The present invention is concerned with providing an ultrasonic catheter which overcomes the "ringdown" problem and also provides an ultrasonic beam which is more effective than the single element beam provided by the prior art.

According to the present invention a catheter including an ultrasonic transducer element positioned in relation to the catheter to emit an ultrasonic signal substantially parallel to or co-axial with the axis of the catheter and a mirror arranged within the catheter to deflect the ultrasonic signal in a substantially radial direction in relation to the axis of the catheter, the path length of the ultrasonic signal within the catheter being such that it overcomes the "ringdown" problem, is characterised by the following features:

a) the transducer includes a substantially circular disc that lies in a substantially diametral plane of the catheter;

b) the mirror comprises a substantially conically shaded reflecting interface located within the catheter at a specified distance from the transducer; and c) the specified distance and the dimensions of the transducer and the conical interface are so selected that the initial path of the emitted ultrasonic signal and the final path of the returning ultrasonic echo signal are contained within the catheter itself so as to overcome the "ringdown" problem.

The term "conical interface" refers to any conical interface between two media or materials such that the effect of the interface is to reflect the ultrasonic beam, or returning echo beam, through an angle sufficient for the beam to exit from the side of the catheter. In practice the conical surface would preferably be inclined at substantially 45° to the catheter axis to thus cause the outgoing ultrasonic beam and the returning echo beam no be turned through substantially 90°.

The "ringdown" distance depends on a number of variables which include the frequency with which the transducer is excited the transducer material, the mounting of the transducer including the backing materials and front layers. Thus it will be a question of detailed design as to exactly what axial distance within the catheter is required between the surface of the transducer and the conical interface.

How the invention may be carried out will now be described, by way of example only, and with reference to the accompanying drawings in which:

FIG. 1 is an enlarged fragmentary perspective view of a first embodiment of the present invention; and FIG. 2 is a view similar to FIG. 1 of a second embodiment of the present invention.

FIG. 1

A catheter 1, in the form of flexible plastic tube 2, has at its distal end 3 (in relation to the surgeon) an arrangement 4 for transmitting ultrasonic signals and receiving their resulting echoes. By means of these signals and echoes, visual representations of the interior of a human organ, for example an artery, may be obtained such as by the arrangement disclosed in our aforementioned two international patent applications.

The ultrasonic arrangement 4 consists of an array of piezo electric elements in the form of segments (5a, 5b, 5c ... etc.) arranged in the form of a circular disc like member 5. Each of the piezo electric transducer elements 5a, 5b, 5c ... etc. may either be discrete elements or alternatively be an integral part of the disc 5 but defined by radially extending slots or cuts in the surface of the disc 5.

The disc 5 is mounted in the end face of a support member 6. Each of the segments 5a, 5b, 5c ... etc. acts as both a transmitter and receiver of the ultrasonic signals and echoes respectively.

A conically shaped reflector surface 7 is located co-axially with respect to the disc 5 and the catheter 1. This reflector surface could be defined in a number of ways. In this embodiment it is formed on the outer surface of a conical member 7a made of metal. Other materials could be used such as Perspex (Registered Trade Mark). The space 8 between the disc 5 and the conical surface of the reflector member 7 is filed with an acoustic transmission fluid. In this embodiment that fluid comprises water but it could be other materials such as a plastic material which acts as a good transmitter of the ultrasonic signals and echoes. In broad terms the conical reflecting surface is defined by two materials having different sound transmission properties so that the interface between them acts as a sound reflector. Therefore, the conical member 7a could in fact be air and the complementary shaped space 8 filled with an appropriate solid material.

An annular acoustic window 9 is provided in the axial circumferential space between the disc 5 and the conical reflector member 7a.

When the ultrasonic transducer elements are in operation the transmitted ultrasonic wave follows the path A, B, C indicated, the returning reflected echoes following a similar return path back to the transducer array (5).

The distance AB+BC, C being at the circumferential outer surface of the catheter (1), is chosen such that it is at least equal to the aforementioned "dead" space and at least equivalent to the "ringdown" time. By this means any item outside the catheter tube (1) can be visualised even if it is in contact with the catheter tube.

The catheter may be provided with a central guide wire 11 in known manner.

FIG. 2

In this second embodiment of the invention is similar to the embodiment of FIG. 1, the basic difference being that the transducer array consists of a separate transmitter and receiver elements whereas in the embodiment of FIG. 1 each of the segments 5a, 5b, 5c . . . etc. acts as both a transmitter and a receiver.

In the embodiment of FIG. 2 there is a single circular disc transmitter piezo electric element 5 and a plurality of separate receiver elements 10a, 10b, 10c . . . etc. arranged in the form of a cylindrical array 10. The other parts of the overall arrangement are similar to the embodiment of FIG. 1 and are indicated with the same reference numerals. The receiving elements 10 are made of a material, such as PVDF which is substantially transparent to the outgoing ultrasonic waves from the disc 5 but opaque to the returning echoes.

With the embodiment of FIG. 2 there is an advantage in separating the transmit and receive functions within the transducer array, as compared with the embodiment of FIG. 1.

Whilst the embodiment of FIG. 1 has the advantage of being a simpler construction than that of the embodiment of FIG. 2 it has the potential operational disadvantage that because the piezo electric elements are segmental in shape they give rise to complications in the processing of the signals generated by them and the signals caused by the echoes received by them.

By separating the functions of transmission and reception the embodiment of FIG. 2 overcomes these disadvantages.

We claim:

1. A catheter including an ultrasonic transducer element positioned in relation to the catheter to emit an ultrasonic signal substantially parallel to or co-axial with the axis of the catheter and a mirror arranged within the catheter to deflect the ultrasonic signal in a substantially radial direction in relation to the axis of the catheter, the path length of the ultrasonic signal within the catheter being such that it overcomes the "ringdown" problem, characterised by the following features:

a) the transducer includes a disc that lies in a substantially diametral plane of the catheter;

b) the mirror comprises a substantially conically shaped reflecting interface located within the catheter at a specified distance from the transducer; and c) the specified distance and the dimensions of the transducer and the conical interface are so selected that the initial path of the emitted ultrasonic signal and the final path of the returning ultrasonic echo signal are contained within the catheter itself so as to overcome the "ringdown" problem.

2. A catheter as claimed in claim 1, in which the disc is substantially circular and divided into a plurality of segments to act as a plurality of transducer elements which in use are adapted to both transmit and receive signals.

3. A catheter as claimed in claim 2, in which the conically shaped reflecting interface is formed by a metal member.

4. A catheter as claimed in claim 2, in which the conically shaped reflecting interface is formed by air.

5. A catheter as claimed in claim 2, in which the conically shaped reflecting interface is formed from plastic sheet.

6. A catheter as claimed in claim 2, in which the space between the disc and the conically shaped reflecting interface is filled with an acoustic transmitting fluid.

7. A catheter as claimed in claim 1, in which the circular transducer disc, in use, acts only as a transmitting element for ultrasonic signals and there are arranged between the disc and the conically shaped reflecting surface a plurality of axially extending transducer elements which are adapted, in use, to act as receivers for the echo signals resulting from the ultrasonic signals transmitted by the disc.

8. A catheter as claimed in claim 7, in which the conically shaped reflecting interface is formed by a metal member.

9. A catheter as claimed in claim 7, in which the conically shaped reflecting interface is formed by air.

10. A catheter as claimed in claim 7, in which the conically shaped reflecting interface is formed from plastic sheet.

11. A catheter as claimed in claim 7, in which the space between the disc and the conically shaped reflecting interface is filled with an acoustic transmitting fluid.

12. A catheter as claimed in claim 1 in which the conically shaped reflecting interface is formed by a metal member.

13. A catheter as claimed in claim 12, in which the space between the disc and the conically shaped reflecting interface is filled with an acoustic transmitting fluid.

14. A catheter as claimed in claim 2, in which the conically shaped reflecting interface is formed by air.

15. A catheter as claimed in claim 14, in which the space between the disc and the conically shaped reflecting interface is filled with an acoustic transmitting fluid.

16. A catheter as claimed in claim 1 in which the conically shaped reflecting interface is formed from plastic sheet.

17. A catheter as claimed in claim 16, in which the space between the disc and the conically shaped reflecting interface is filled with an acoustic transmitting fluid.

18. A catheter as claimed in claim 1 in which the space between the disc and the conically shaped reflecting interface is filled with an acoustic transmitting fluid.

19. A catheter as claimed in claim 18, in which the transmitting fluid comprises water.

\* \* \* \* \*

UNITED STATES PATENT AND TRADEMARK OFFICE
CERTIFICATE OF CORRECTION

PATENT NO.  : 5,465,726
DATED       : November 14, 1995
INVENTOR(S) : Robert J. Dickinson and Richard I. Kitney It is certified that error appears in the above-indentified patent and that said Letters Patent is hereby corrected as shown below:

Column 1, line 22, after "This" insert --is--;
         line 61, change "shaded" to --shaped--.

Column 4, line 43, change "2" to --1--.

Signed and Sealed this

Twenty-seventh Day of February, 1996

Attest:

BRUCE LEHMAN

Attesting Officer        Commissioner of Patents and Trademarks